United States Patent [19]

Storz

[11] Patent Number: 5,048,508
[45] Date of Patent: Sep. 17, 1991

[54] ENDOSCOPE HAVING SEALED SHAFT

[76] Inventor: Karl Storz, Auf dem Schildrain 39, 7200 Tuttlingen, Fed. Rep. of Germany

[21] Appl. No.: 566,580

[22] Filed: Aug. 13, 1990

[30] Foreign Application Priority Data

Dec. 23, 1989 [DE] Fed. Rep. of Germany ....... 3942905

[51] Int. Cl.$^5$ .............................................. A61B 1/00
[52] U.S. Cl. ....................................................... 128/4
[58] Field of Search ................................ 128/4, 5, 6, 7

[56] References Cited

U.S. PATENT DOCUMENTS

| | | | |
|---|---|---|---|
| 4,167,939 | 9/1979 | Storz | 128/4 |
| 4,630,598 | 12/1986 | Bonnet | 128/7 |
| 4,653,476 | 3/1987 | Bonnet | 128/4 |
| 4,700,694 | 10/1987 | Shisido | 128/6 |
| 4,784,118 | 11/1988 | Fantone | 128/6 |
| 4,944,287 | 7/1990 | Takahashi et al. | 128/4 |

Primary Examiner—William H. Grieb
Attorney, Agent, or Firm—William A. Drucker

[57] ABSTRACT

An endoscope having an edoscope shaft, a periscope, optics removably secured to the endoscope shaft and separable from the endoscope shaft and an instrument channel having an apertured cap through which treatment instruments are introduced into the instrument channel under visual control via the optics. The endoscope shaft has a hollow interior, a substantially kidney-shaped cross-section with a substantially semicircular upper surface portion for partial extenral reception of a catheter in the semicircular upper surface and a lower surface within the hollow interior retaining the periscope thereon.

4 Claims, 2 Drawing Sheets

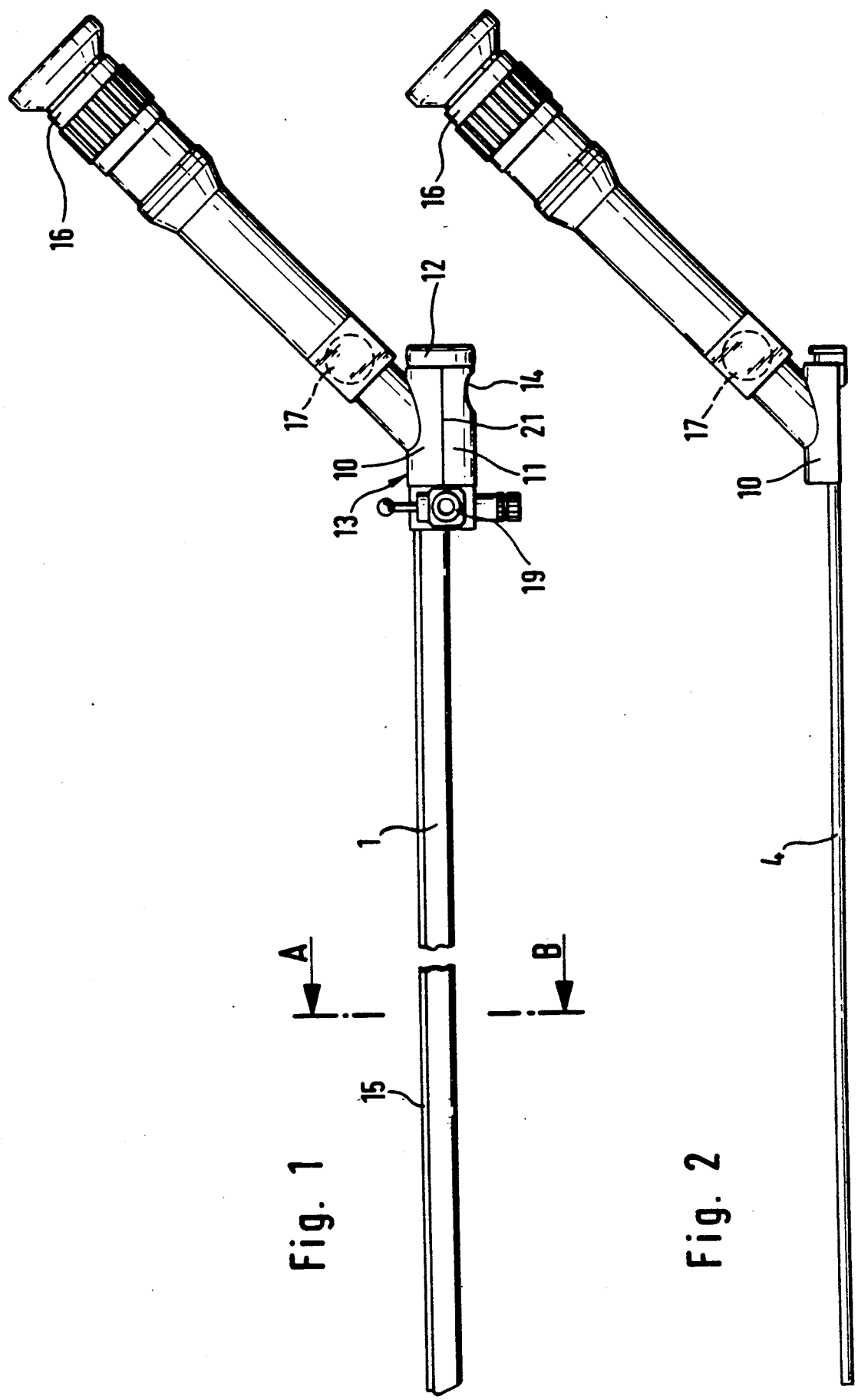

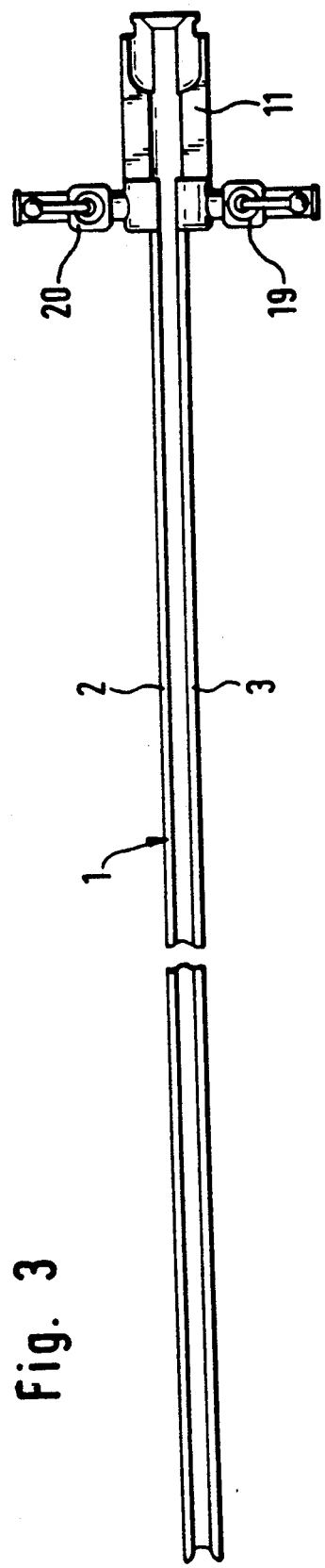
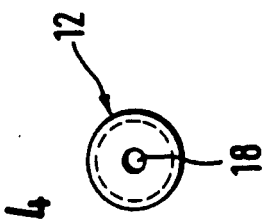
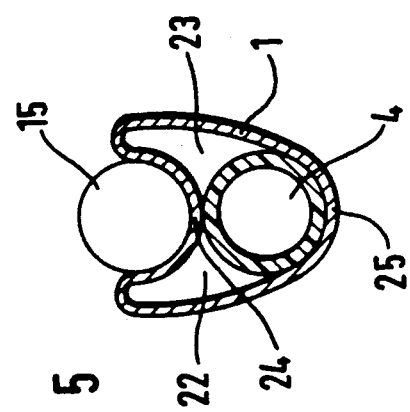
Fig. 3
Fig. 4
Fig. 5

ENDOSCOPE HAVING SEALED SHAFT

BACKGROUND OF THE INVENTION

1. Field of the Invention

The invention relates to an endoscope.

2. Brief Description of the Prior Art

The prior art discloses an endoscope, in which the endoscope shaft, in section at right angles to its longitudinal direction, is constructed in upwardly open, U-shaped manner and in which offsets or shoulders are provided on the two legs of this U-shaped construction, which serve as sealing faces for the periscope. Thus, after the thick treatment instrument, e.g. a balloon catheter, has been inserted in the bladder, it can remain in situ under visual control, while the endoscope is drawn out of the body cavity.

In another known endoscope of this type (No. 270339 of Karl Storz GmbH & Co., Tuttlingen, Germany), the endoscope shaft serves not only for the passage of different treatment instruments, but also for rinsing a body cavity and for this purpose a rinsing device with an inflow and an outflow is positioned at the patient-remote end of the endoscope shaft.

In addition, in medical endoscopy, both rectoscopes and laryngoscopes are known which can undergo lengthwise disassembly and comprise two tube halves which cannot be sealed against one another and which are therefore unsuitable for use in the bladder with a liquid filling.

SUMMARY OF THE INVENTION

The present invention is based on the problem of finding a construction of the aforementioned type, which permits easier handling and much better sealing.

Briefly, in accordance with the present invention, the endoscope shaft is completely closed at the top instead of being open, so that the interior is completely and reliably sealed. It can therefore be used for receiving the rinsing device and for receiving the periscope. The catheter is now fixed in the semicircular outer receptacle, which also facilitates handling.

The inner area of the endoscope, left free with respect to the periscope, is used in the control area for rinsing with water to maintain the inner rinsing device absolutely tightly within the endoscope shaft.

The endoscope shaft and the catheter are dimensioned so that the catheter can be easily fixed from the outer shaft area whereby the catheter can easily be removed from the endoscope shaft and the necessary hold between the two parts is ensured by a clamp connection.

BRIEF DESCRIPTION OF THE DRAWINGS

The invention is described in greater detail hereinafter relative to a non-limitative embodiment and the attached drawings, wherein:

FIG. 1 is a side view of the preferred embodiment.

FIG. 2 is a side view of the dismantled periscope with the eyepiece.

FIG. 3 is a plan view of the endoscope shaft only.

FIG. 4 is a plan view of the rubber cap only.

FIG. 5 is a section along line A-B of FIG. 1 on a larger scale.

DESCRIPTION OF THE PREFERRED EMBODIMENT

FIG. 1 shows the endoscope shaft 1, to which is initially connected a thickened portion with the two rinsing cocks 19, 20, whereof only 19 is visible in this side view. Also shown is the head 13, which is subdivided by the separating line 21 into a lower part 11 forming the patient-remote end of the endoscope shaft 1, while the upper part 10 is constructed in one piece with the periscope 4 in the lower region and the eyepiece 16, as is clearly visible in FIG. 2. These two parts 10 and 11 are held together by the rubber cap 12 at the patient-remote end. The recess 14 for the easier manual dismantling of the rubber cap can be seen. It is also possible to see the catheter 15, in which area the catheter projects above the endoscope shaft, as will be explained in detail hereinafter.

FIG. 2 shows the periscope 4 only, which is located in the lower area of the endoscope shaft 1 according to FIG. 1, but is not visible there because it is completely enveloped by the latter. To this is connected the end of the periscope 10 mentioned relative to FIG. 1 and which is here positioned in the lower part of the head 13 and, with the sloping eyepiece 16, forms a unit. In the lower part of the eyepiece there is provided in known manner a light guide connection 17 (shown in phantom).

FIG. 3 is a plan view of the kidney-shaped endoscope shaft 1 with the two rinsing cocks 19 and 20, in which the, patient-remote end of the endoscope shaft is constructed as the lower part of the head 13 according to FIG. 1.

FIG. 4 shows the known rubber cap 12 with a central hole 18, which is dimensioned in such a way that the balloon catheter or similar treatment instrument to be introduced there is sealed with respect to the cap 12, which is known per se. However, it now has the additional function according to FIG. 1 of holding together the two halves 10 and 11 of the head.

Finally, FIG. 5 shows the section along line A-B of FIG. 1. It is possible to see that the endoscope shaft 1 is kidney-shaped toward the top without an opening. In the central, upper area 24 of the endoscope shaft, it is possible to see a roughly semicircular outer receptacle for the catheter 15. Preferably the dimensioning of the catheter and the downwardly directed semicircular bulge 24 is selected in such a way that the catheter 15 can be easily fixed in the bulge 24.

The periscope 4 is positioned below the catheter 15 in the completely closed interior of the endoscope shaft 1, so that there is no need for a special seal between the periscope 4 and the cavities 22, 23 of the endoscope shaft which are used for water rinsing purposes. The periscope 4 can once again be provided with a filling tube, which has an elastic coating. Between the latter and the periscope and the bulge 24, a seal can be provided so that e.g. the left-hand cavity 22 of the endoscope shaft can be used under pressure for passing on the rinsing water, while the dirty water is sucked off through the cavity 23.

In the bottom region 25 of the endoscope shaft, the semicircular receptacle is naturally adapted to the external diameter of the periscope.

The operation of the object of the invention will now be described. The endoscope according to the invention is more particularly constructed as a cysto-urethroscope and is inserted into the urethra by the surgeon in the usual way and need not be explained because it is well known.

A thick treatment instrument, e.g. a balloon catheter is then introduced through the hole 18 in the rubber cap 12 under visual control by eyepiece 16. Rinsing has taken place beforehand through the two rinsing cocks 19, 20.

The endoscope is now removed, while leaving the balloon catheter in place. Firstly, the rubber cap 12 is removed to the right, facilitated by inserting a finger in the recess 14. It must be ensured that there is no slipping of the balloon catheter and that it is firmly secured so that there is no relative movement between the catheter and the endoscope shaft. After the removal of the cap 12 the periscope 4 is drawn out to the right together with the eyepiece 16, this being possible because, after releasing the rubber cap 12, there is no further locking means between the parts 10 and 11. The endoscope shaft 1 is now drawn out of the body cavity, but the balloon catheter 15 remains in situ. For this purpose the balloon catheter must be firmly held and the endoscope shaft is drawn slightly downwards, so that the balloon catheter 15 slips upwards out of its fixture. The front part of the balloon catheter 15 near the patient can, for the time being, remain in the receptacle 24. This means that the end 11 of the shaft 1 is moved downwards slightly, which is easily brought about because the catheter 15 easily slides out of the receptacle 24.

The invention is not restricted to the represented embodiment and those skilled in the art can in fact make numerous modifications within the scope of the claims.

I claim:

1. An endoscope, comprising:
   (a) an endoscope shaft;
   (b) a periscope;
   (c) optics removably secured to said endoscope shaft and separable from said endoscope shaft; and
   (d) an instrument channel having an apertured cap through which treatment instruments are introduced into said instrument channel under visual control via said optics;
   (e) said endoscope shaft having:
      (i) a hollow interior;
      (ii) a substantially kidney-shaped cross-section with a substantially semicircular upper surface portion for partial external reception of a catheter in said semicircular upper surface; and
      (iii) a lower surface within said hollow interior retaining said periscope thereon.

2. The endoscope of claim 1 further including means to provide rinsing water in said endoscope shaft interior external to said periscope.

3. The endoscope of claim 1 further including a catheter, said endoscope shaft and said catheter dimensioned for easy fixing from the exterior of said endoscope shaft.

4. The endoscope of claim 2 further including a catheter, said endoscope shaft and said catheter dimensioned for easy fixing from the exterior of said endoscope shaft.

* * * * *